United States Patent [19]

Kobayashi et al.

[11] Patent Number: 4,806,578

[45] Date of Patent: Feb. 21, 1989

[54] PROCESS FOR PRODUCING HIGHLY ABSORPTIVE RESIN

[75] Inventors: Takatoshi Kobayashi; Takahiro Ohya, both of Wakayama, Japan

[73] Assignee: KAO Corporation, Tokyo, Japan

[21] Appl. No.: 896,720

[22] Filed: Aug. 15, 1986

[30] Foreign Application Priority Data

Aug. 30, 1985 [JP] Japan ................................. 60-191100

[51] Int. Cl.$^4$ ................................................ C08K 3/20
[52] U.S. Cl. ..................................... 523/402; 525/119
[58] Field of Search ......................... 523/402; 525/119

[56] References Cited

U.S. PATENT DOCUMENTS 4,666,975 5/1987 Yamasaki et al. .................... 525/119
4,666,983 5/1987 Tsubakimoto et al. ............. 525/119

Primary Examiner—Joseph L. Schofer
Assistant Examiner—Bernard Lipman
Attorney, Agent, or Firm—Birch, Stewart, Kolasch & Birch

[57] ABSTRACT

A highly absorptive resin is produced by crosslinking a starting polymer being hydrophilic, having a carboxylic group or a carboxylate group, having a water content of 10 to 40 percent by weight, with a polyglycidyl ether having 4 or more epoxy groups, being water-soluble. The resin has a long life in absorption.

7 Claims, No Drawings

PROCESS FOR PRODUCING HIGHLY ABSORPTIVE RESIN

The present invention relates to a process for producing a water-insoluble water-absorbent material capable of absorbing a large amount of an aqueous liquid and keeping the same stable. More particularly, the invention relates to a process for producing a water-absorbent material having excellent salt resistance and a high water absorption rate, these properties being stable and unchanged with time.

STATEMENT OF PRIOR ARTS

Though various water-absorbent materials such as paper or pulp have been used in the production of sanitary materials (such as a sanitary napkin or a paper diaper) and in the agricultural field, these waterabsorbent materials have only a low water-absorbing capacity and a great part of water once absorbed therein is pressed out upon application of pressure.

Other absorbent materials such as hydrolyzates of starch-acrylonitrile graft polymers, modified cellulose ethers and hydrolyzates of methyl acrylate/vinyl acetate copolymers were proposed as substitutes for said materials recently and they were further improved. However, their water-absorbent capacities and water-absorption rates are yet insufficient and thus, no satisfactory water-absorbent materials have been obtained as yet.

The inventors previously proposed water-absorbent materials having a high water-absorbing capacity (see the specification of Japanese Patent Publication No. 30710/1979) and further improved water-absorbent materials (see the specifications of Japanese Patent Laid-Open Nos. 62665/1984 and 1204/1985). However, also these water-absorbent materials have problems that the prevention of changes in the water-absorbing capacity of them with time is difficult and that the capacity of them is reduced seriously during repeated use (i.e. during water absorption—drying—water absorption). Under these circumstances, the development of a water-absorbent material having a high water absorbing capacity which does not deteriorate with time has eagerly been demanded.

SUMMARY OF THE INVENTION

After intensive investigations made for the purpose of producing a reusable polymer free of the above-mentioned defects and having an excellent salt resistance and a high water absorption rate which are unchanged with time, the inventors have found that a polymer obtained by crosslinking a hydrous hydrophilic polymer having a water content controlled in a specified range with a specified crosslinking agent has an excellent water absorption and particularly excellent salt resistance and a water absorption rate. The present invention has been completed on the basis of this finding.

According to the invention, a highly absorptive resin is produced by crosslinking a starting polymer being hydrophilic, having a carboxylic group or a carboxylate group, and having a water content of 10 to 40 percent by weight, with a water soluble polyglycidyl ether having 3 or more epoxy groups, being. The resin has a long life for absorption. In order to attain the invention effectively it may be practical to adjust a water content of the starting polymer by dehydration in advance of the crosslinking step. It is preferable that the starting polymer is obtained by polymerizing a hydrophilic monomer having a carboxylic group or a carboxylate group with a water-soluble initiator by the reversed phase suspension polymerization. In addition, the invention provides the resin obtained by the process.

The present invention provides a process for producing a highly water-absorbent resin having excellent durability characterized in that a hydrous hydrophilic polymer having a carboxyl (or carboxylate) group and a water content controlled to 10 to 40 wt. % is crosslinked with a water-soluble polyglycidyl ether compound having three or more epoxy groups.

Most conventional processes for producing a water-absorbent polymer comprise slightly crosslinking a water-soluble polymer to make it water-insoluble. For the crosslinking, the following processes have been proposed:

(1) a process wherein the production conditions are optimized for effecting self-crosslinking, and (2) a process wherein a crosslinking agent is added in the course or after completion of the polymerization to effect crosslinking.

Though some of the water-absorbent polymers thus obtained have excellent properties, not all of the demanded properties can be satisfied. The properties required of the water-absorbent polymers are (1) water absorption, (2) water absorption rate and (3) gel strength. However, the following relationship has been recognized usually among these properties:

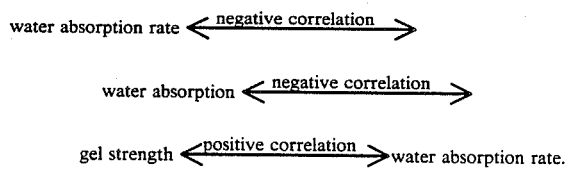

The ordinary water-absorbent polymers have well-balanced properties and, therefore, the respective properties are sacrificed to some extent.

An object of the present invention is to overcome the above-mentioned defects to thereby provide a process for producing an epochal water-absorbent polymer which satisfies the properties required of the highly water-absorbent polymers having properties which are stable and unchanged with time.

It is important for attaining the object of the present invention that the hydrophilic polymer has a carboxyl (or carboxylate) group, that the water content of the hydrous hydrophilic polymer is within a specified range and that a specified crosslinking agent is used.

The kinds of the hydrophilic polymers used in the present invention is not limited so far as each structural unit thereof has a carboxyl (or carboxylate) group and the polymerization processes for producing them are not limited, either. Examples of preferred hydrophilic polymers usable in the present invention include polysodium acrylate produced by the reversed phase suspension polymerization process disclosed in the specifications of Japanese Patent Publication No. 30710/1979 and Japanese Patent Laid-Open No. 26909/1981, polysodium acrylate produced by aqueous solution polymerization (adiabatic or thin film polymerization) disclosed in the specification of Japanese Patent Laid-Open No. 133413/1980 and starch-sodium acrylate graft polymers disclosed in the specification of Japanese Patent Publication No. 46199/1978. Addition of a crosslinking agent in the production of said polymers does not damage the effects of the present invention, if it is in only a very small amount. To impart prolonged stability, which is one of the characteristic features of the present invention, to the polymer, it is desirable that the polymer be self-crosslinked. The degree of neutralization of the polymer is preferably in the range of 60 to 90 molar % from the viewpoints of the prolonged stability of the water-absorbent polymer and the water absorption—drying—water absorption cycles, since an epoxy compound is used as the crosslinking agent and the crosslinked structure has an ester bond.

A dehydration step is necessary usually after the preparation of the polymer, since one of the requisites of the present invention comprises control of the water content of the hydrous polymer. Therefore, a polymer produced by the reversed phase suspension polymerization process is desirable from the viewpoint of the workability or the like. Examples of the polymers having a carboxyl (or carboxylate) group in the structural unit thereof include usually polyacrylic acid, polymethacrylic acid and salts thereof. They are preferably used in the process of the present invention. Copolymers produced by copolymerizing acrylic or methacrylic acid with a comonomer such as maleic acid, itaconic acid acrylamide, 2-acrylamido-2-methylpropanesulfonic acid, 2-(meth)acryloylethanesulfonic acid or 2-hydroxyethyl (meth)acrylate in such a manner that the properties of the water-absorbent polymer are not damaged may be used in the process of the present invention.

When employing the reversed phase suspension polymerization process, an aqueous solution of a hydrophilic monomer having a carboxyl (or carboxylate) group is subjected to the reversed phase suspension polymerization with a protective colloid in a non-aqueous solvent. The protective colloids usable in this process include sorbitan fatty acid esters such as sorbitan monostearate and monolaurate; cellulose ethers such as ethylcellulose and benzylcellulose; cellulose esters such as cellulose acetate, cellulose butyrate and cellulose acetate butyrate; and high-molecular dispersants such as maleinized polybutadiene, maleinized polyethylene and maleinized α-olefins. They may be used either alone or in the form of a mixture of them. Examples of the non-aqueous solvents include aliphatic hydrocarbons such as hexane, heptane and octane; alicyclic hydrocarbons such as cyclohexane, methylcyclohexane and decalin; aromatic hydrocarbons such as benzene, toluene and xylene; and halogenated hydroarbons such as chlorobenzene, bromobenzene and dichlorobenzene.

Another requisite of the present invention is that the water content of the hydrous hydrophilic polymer to be crosslinked in the presence of the crosslinking agent is controlled in a specified range. Processes for producing water-absorbent polymers wherein the crosslinking reaction is carried out after completion of the polymerization have been known. For example, a process wherein a polyacrylic acid salt is crosslinked in a solvent mixture of water and a hydrophilic organic solvent is disclosed in the specification of Japanese Patent Laid-Open No. 131608/1981 and a process wherein polyacrylic acid (or its salt) is crosslinked in the presence of water is disclosed in the specification of Japanese Patent Publication No. 28505/1982.

However, the water content of said hydrous polymers is 50 wt. % or higher and, particularly, the latter polymer has a water content of 70 wt. % or higher. With such a high water content, the effects of the present invention cannot be exhibited.

Usually, a hydrophilic polymer is obtained by carrying out the polymerization in an aqueous solution having a monomer concentration of 45 wt. % or less, i.e. a water content of 55 wt. % or higher. Therefore, in carrying out the process of the present invention, the water content of the hydrophilic polymer produced by an ordinary process must be controlled.

It is indispensable in the present invention that the water content be in the range of 10 to 40 wt. %, preferably 15 to 35 wt. % based on the total amount of the hydrous hydrophilic polymer. When the water content of the hydrophilic polymer is outside the above-mentioned range, the water-absorption and/or water absorption rate are(is) low and the remarkable effects of the present invention cannot be obtained. The intended effects can be obtained according to the present invention by controlling the water content in the above-mentioned range by, for example, concentrating the polyacrylic acid obtained by the reversed phase suspension polymerization.

Still another requisite of the present invention is a crosslinking agent. A characteristic feature of the present invention resides in a crosslinking agent capable of improving the water-absorbing capacity and maintaining said capacity unchanged with time. The characteristic crosslinking agent used in the present invention is a water-soluble polyglycidyl ether compound having at least three epoxy groups as functional groups reactive with the carboxyl (or carboxylate) group in the molecule. Examples of the crosslinking agents include sorbitol polyglycidyl ether, pentaerythritol polyglycidyl ether and polyglycerol polyglycidyl ether. From the viewpoint of the prolonged stability of the water-absorbent resin, a tetrafunctional or higher functional polyglycerol polyglycidyl ether is preferred. A difunctional diglycidyl ether is not preferred in the present invention, since the prolonged stability of the product is low and the capacity of the polymer is extremely low in case the swollen polymer after absorption of water is dried and then water is absorbed therein, though the water absorbing capacity is improved by using the difunctional ether.

The amount of the crosslinking agent which varies depending on the kinds of the crosslinking agent and polymer is usually in the range from 0.01 to 5.0 wt. %. When the amount of the crosslinking agent is less than 0.01 wt. %, the effects thereof cannot be exhibited sufficiently and, on the contrary, when it exceeds 5.0 wt. %, the crosslinking density is increased to reduce the water absorption unfavorably.

Various processes have been proposed for carrying out the reaction in the presence of the crosslinking agent. When the polymer produced by the reversed phase suspension polymerization process is used, the crosslinking agent is added to a suspension of the hydrophilic polymer having a water content controlled within the range of the present invention in an organic solvent and then a heat treatment is effected. When the polymer produced by the thin film polymerization process is used, the resulting polymer gel is cracked, the water content thereof is controlled by drying, the polymer is placed in a kneader, the crosslinking agent is added thereto and the mixture is heat-treated to effect the crosslinking reaction. For carrying out the crosslinking reaction smoothly, it is preferred to effect the reaction under heating to a temperature in the range of 40° to 150° C.

The process of the present invention makes it possible to obtain the water-absorbent material having an excellent salt resistance and a high water absorption rate, which is stable and unchanged with time and which can be used repeatedly while the stability is kept unchanged. The water-absorbent resin produced according to the present invention can be used quite advantageously as an agricultural water-retaining agent and a water absorbent for sanitary materials. The high water-absorbent polymer produced by the process of the present invention is usable advantageously in the production of paper diapers where rapid absorption of a large amount of urine is required and sanitary napkins where absorption of blood is required. These products can be used without causing problems of "leakage" and "feelings of unpleasantness".

[EXAMPLES]

The following examples and comparative examples will further illustrate the present invention, which by no means limit the invention. In the examples, percentages are given by weight unless otherwise stated.

In the following examples and comparative examples, the water absorption was determined as follows: about 1 g of the polymer was dispersed in a large excess of physiological saline to swell it sufficiently. It was then filtered through an 80-mesh metal gauze and the obtained swollen polymer was weighed. The weight (W) thus determined was divided by the initial weight of the polymer ($W_o$) to determine the water absorption.

Namely, the water absorption (g/g) is represented by $W/W_o$. The water absorption rate was represented by the amount of phosiological saline absorbed in 0.5 g of the polymer in 10 min.

EXAMPLES 1 to 3

230 ml of cyclohexane and 0.5 g of ethylcellulose T-50 (a product of Hercules) were placed in a 500-ml four-necked, round-bottom flask provided with a stirrer, reflux condenser, dropping funnel and nitrogen gas-inlet tube and heated to 75° C. Separately, 30 g of acrylic acid was neutralized with a solution of 13.4 g of sodium hydroxide in 39 g of water in an Erlenmeyer flask. The aqueous monomer solution had a monomer concentration of 45% (water content of 55%). Then, 0.1 g of potassium persulfate was dissolved therein. The aqueous monomer solution was added dropwise to the mixture in the above-mentioned four-necked flask over a period of 1.5 h in a nitrogen atmosphere and the reaction mixture was kept at 70° to 75° C. for 0.5 h to complete the polymerization. Thereafter, the water content of the polymer suspended in cyclohexane was adjusted to 35%, 27% and 20% by azeotropic dehydration while cyclohexane was refluxed. An aqueous solution of 0.05 g of polyglycerol polyglycidyl ether (Denacol EX-512; a product of Nagase Sangyo Co.) in 1 ml of water was added to each of them at 73° C. and the mixture was kept at that temperature for 2 h. Cyclohexane was removed and the polymer was dried at 80° to 100° C. under reduced pressure to obtain a water-absorbent polymer.

EXAMPLE 4

The polymerization was effected in the same manner as in Example 1 except that ethylcellulose T-50 was replaced with 1.8 g of sorbitan monostearate. After completion of the polymerization, the water content of the polymer was adjusted to 22% by azeotropic dehydration and then a solution of 0.07 g of polyglycerol polyglycidyl ether (Denacol EX-521; a product of Nagase Sangyo Co.) in 1 ml of water was added thereto at 73° C. and the mixture was kept at that temperature for 3 h. Cyclohexane was removed and the polymer was dried at 80° to 100° C. under reduced pressure to obtain a water-absorbent polymer.

EXAMPLE 5

The polymerization was effected in the same manner as in Example 4 except that the concentration of the monomer in the aqueous solution thereof was 35% and 0.003 g of N,N'-methylenebisacrylamide was further added to the reaction system. After completion of the polymerization, the water content of the polymer was adjusted to 27%. A solution of 0.06 g of polyglycerol polyglycidyl ether (Denacol EX-512) in 1 ml of water was added thereto at 60° C. and the mixture was kept at that temperature for 3 h. Cyclohexane was removed and the polymer was dried at 80° to 110° C. under reduced pressure to obtain a water-absorbent polymer.

EXAMPLE 6

30 g of acrylic acid was neutralized with a solution of 13.4 g of sodium hydroxide in 39 g of water. The concentration of the monomer in the aqueous solution thereof was 45%. Then, 0.1 g of sodium persulfate was dissolved therein. The obtained aqueous monomer solution was poured between two Teflon plates and thin film polymerization was carried out at 60° C. for 3 h. The polymer gel thus obtained was cut into 3 mm pieces and dried in a hot air dryer until the water content thereof was reduced to 30%. The obtained product was placed in a kneader. A solution of 0.06 g of polyglycerol polyglycidyl ether (Denacol EX-512) in 1 ml of water was sprayed thereon and the product was left to stand at 70° C. for 1 h and dried at 70° to 80° C. under reduced pressure. The polymer thus obtained was pulverized to obtain a water-absorbent polymer having a median particle diameter of 100 to 250 μm.

COMPARATIVE EXAMPLE 1

The polymerization was effected in the same manner as in Example 1 except that 0.06 g of polyglycerol polyglycidyl ether (Denacol EX-512) was added to the aqueous monomer solution and the crosslinking was effected simultaneously with the polymerization. After completion of the polymerization, cyclohexane was removed and the polymer was dried at 80° to 100° C. under reduced pressure to obtain a water-absorbent polymer.

COMPARATIVE EXAMPLE 2

The polymerization was effected in the same manner as in Example 1 except that the aqueous solution of the crosslinking agent was added after completion of the polymerization (water content of the hydrous polymer: 55%) and the mixture was kept at 73° C. for 1 h. After completion of the crosslinking reaction, cyclohexane was removed and the polymer was dried at 80° to 100°

C. under reduced pressure to obtain a water-absorbent polymer.

COMPARATIVE EXAMPLE 3

The polymerization was effected in the same manner as in Example 1 except that the aqueous solution of the crosslinking agent was added after adjusting the water content of the polymer to 45% by the azeotropic dehydration and the mixture was kept at 60° C. for 2 h. After completion of the crosslinking reaction, cyclohexane was removed and the polymer was dried at 80° to 100° C. under reduced pressure to obtain a waterabsorbent polymer.

COMPARATIVE EXAMPLE 4

The polymerization was effected in the same manner as in Example 1. Then, cyclohexane was removed and the product was dried at 70° to 80° C. under reduced pressure. The water content of the polymer was 7%. The polymer was dispersed again in cyclohexane to obtain a suspension. The aqueous solution of the crosslinking agent was added thereto and the mixture was kept at 70° C for 1 h. Then, cyclohexane was removed and the polymer was dried at 80° to 100° C. under reduced pressure to obtain a water-absorbent polymer.

COMPARATIVE EXAMPLEs 5 to 7

The polymerization was effected in the same manner as in Example 1 except that a solution of an equal epoxy equivalent (0.03 g) of ethylene glycol diglycidyl ether (Denacol EX-810; a product of Nagase Sangyo Co.) in 1 ml of water was added in place of polyglycerol polyglycidyl ether at 73° C. while the water content of the polymer was adjusted to 35%, 27% or 20%. Then, the same treatment as in Example 1 was repeated.

The water absorptions and water absorption rates of the water-absorbent polymers obtained in Examples 1 to 6 and Comparative Examples 1 to 7 are shown in Table 1. Further, the water absorptions and water absorption rates of the polymers obtained by swelling these polymers 100-fold by volume with ion-exchanged water and then drying them at 80° C. under 40 mmHg are shown in Table 2. In another test, the polymers were swollen 200-fold by volume with ion-exchanged water, placed on an inclined surface and exposed to outdoor light at room temperature and the time (days) necessitated until the fluidity of the polymer appeared was measured to obtain the results shown in Table 2.

TABLE 1

| | | Water-absorbing capacity | |
|---|---|---|---|
| | | Water absorption (g/g) | Water absorption rate (ml) |
| Examples | 1 | 68 | 25.8 |
| | 2 | 72 | 27.2 |
| | 3 | 82 | 27.5 |
| | 4 | 78 | 26.3 |
| | 5 | 76 | 24.7 |
| | 6 | 65 | 24.4 |
| Comp. Exs. | 1 | 53 | 11.9 |
| | 2 | 48 | 11.4 |
| | 3 | 55 | 10.7 |
| | 4 | 59 | 10.8 |
| | 5 | 65 | 24.6 |
| | 6 | 70 | 25.5 |
| | 7 | 77 | 26.1 |

TABLE 2

| | | Absorption capacity after swelling and drying[1] | | Shelf stability[2] (days) |
|---|---|---|---|---|
| | | Water absorption (g/g) | Water absorption rate (ml) | |
| Examples | 1 | 65 | 26.2 | 20 |
| | 2 | 76 | 26.4 | 19 |
| | 3 | 84 | 27.4 | 18 |
| | 4 | 81 | 25.8 | 19 |
| | 5 | 75 | 25.4 | 20 |
| | 6 | 60 | 25.6 | 18 |
| Comp. Exs. | 1 | 54 | 9.6 | 25 |
| | 2 | 68 | 7.7 | 20 |
| | 3 | 58 | 10.5 | 24 |
| | 4 | 57 | 9.8 | 24 |
| | 5 | 84 | 9.6 | 3 |
| | 6 | 90 | 10.3 | 3 |
| | 7 | disolved | — | 1 |

[1] Water-absorbing capacity of water-absorbent resin swollen 100-fold by volume with ion-exchanged water and dried at 80° C. under 40 mmHg.
[2] Fluidity of the resin swollen 200-fold by volume with ion-exchanged water examined by exposure to the sunlight at room temperature (the number of days necessitated until the sample placed on an inclined surface at 30° began to flow).

It is apparent from Tables 1 and 2 that the water-absorbent polymers of the present invention have a high water-absorption capacity and that the properties of these polymers can be kept consistent and the polymers were durable to repeated use.

As described in the above examples, the highly durable, highly water-absorbent resins obtained by the process of the present invention have high salt resistance and water absorption rates and their properties are unchanged with time or by repeated use. They are quite usable as an agricultural water-retaining agent and as a water- or blood-absorbent in sanitary materials.

When the resins of the present invention are used as the agricultural water-retaining agent, they can be used for a long period of time, since they are stable during repeated cycles of water retention—release of water—water retention. Further, said stability is not deteriorated by the reuse under conditions comprising a high temperature and a low humidity.

In the field of sanitary materials, the resins can be used advantageously in the production of paper diaper and sanitary napkin, since the properties of them can be kept consistent even after the absorption of water of blood.

The embodiments of the invention in which an exclusive property or privilege is claimed are defined as follows:

1. A process for producing a highly absorptive resin, which comprises the step of crosslinking a hydrous hydrophilic starting polymer, having a carboxylic acid group or a carboxylate group thereof, and having a water content of 10 to 40 percent by weight, with a water soluble polyglycidyl ether having at least 4 expoxy groups.

2. A process as claimed in claim 1, which comprises the step of adjusting said water content of the starting polymer by dehydration.

3. A process as claimed in claim 1, in which said polyglycidyl ether is used in an amount of 0.01 to 5 percent by weight per weight of said hydrophilic starting polymer.

4. A process as claimed in claim 1, which further comprises the step of obtaining the starting polymer by polymerizing a hydrophilic monomer having a carboxylic group or a carboxylate group with a water-soluble initiator by reversed phase suspension polymerization.

5. A process as claimed in claim 1, in which said starting polymer is a polymer or copolymer of acrylic acid or an alkali metal acrylate.

6. A highly absorptive resin obtained by the process as claimed in claim 1.

7. A process as claimed in claim 1, wherein said polyglycidyl ether is selected from the group consisting of sorbitol polyglycidyl ether, pentaerythritol polyglycidyl ether and polyglycerol polyglycidyl ether.

* * * * *